United States Patent
Marino

(10) Patent No.: US 6,406,175 B1
(45) Date of Patent: Jun. 18, 2002

(54) BONE CEMENT ISOVOLUMIC MIXING AND INJECTION DEVICE

(76) Inventor: James F. Marino, 2620 St. Tropez Pl., La Jolla, CA (US) 92037

( * ) Notice: Subject to any disclaimer, the term of this patent is extended or adjusted under 35 U.S.C. 154(b) by 0 days.

(21) Appl. No.: 09/564,827

(22) Filed: May 4, 2000

(51) Int. Cl.[7] .................................................. B01F 13/06
(52) U.S. Cl. ........................ 366/130; 366/139; 366/256; 222/246
(58) Field of Search .................................. 366/130, 139, 366/255–260, 332, 333; 222/246

(56) References Cited

U.S. PATENT DOCUMENTS

| | | | |
|---|---|---|---|
| 4,277,184 A | 7/1981 | Solomon | 366/139 |
| 4,458,733 A | 7/1984 | Lyons | 141/1 |
| 4,676,655 A * | 6/1987 | Handler | |
| 4,799,801 A | 1/1989 | Bruning | 366/255 |
| 4,973,168 A | 11/1990 | Chan | 366/139 |
| 5,100,241 A | 3/1992 | Chan | 366/139 |
| 5,114,240 A | 5/1992 | Kindt-Larsen et al. | 366/129 |
| 5,145,250 A | 9/1992 | Planck et al. | 366/8 |
| 5,571,282 A | 11/1996 | Earle | 366/139 |
| 5,588,745 A | 12/1996 | Tanaka et al. | 366/130 |
| 5,951,160 A * | 9/1999 | Ronk | |
| 5,961,211 A | 10/1999 | Barker et al. | 366/182.3 |
| 5,975,751 A | 11/1999 | Earle | 366/139 |

* cited by examiner

Primary Examiner—Charles E. Cooley
Assistant Examiner—David Sorkin
(74) Attorney, Agent, or Firm—Henri J. A. Charmasson; John D. Buchaca

(57) ABSTRACT

A device for preparing and injecting a polymeric bone cement under sterile, isobaric and isovolumic conditions includes a cylindrical vessel holding a volume of polymeric powder and a disk agitator mounted on a shaft passing through an aperture in a proximal end wall of the vessel and extending beyond the agitator though a delivery port in an opposite wall of the vessel. A piston can be selectively coupled to the disk in order to inject the contents of the vessel through the outlet port. The device can be packaged in a sterilized, evacuated envelope. The cement is ejected by breaking off a distal, tubular section of the shaft and mounting the broken off section over an external bushing surrounding the outlet port and moving the piston toward the outlet port to expel the contents of vessel.

11 Claims, 3 Drawing Sheets

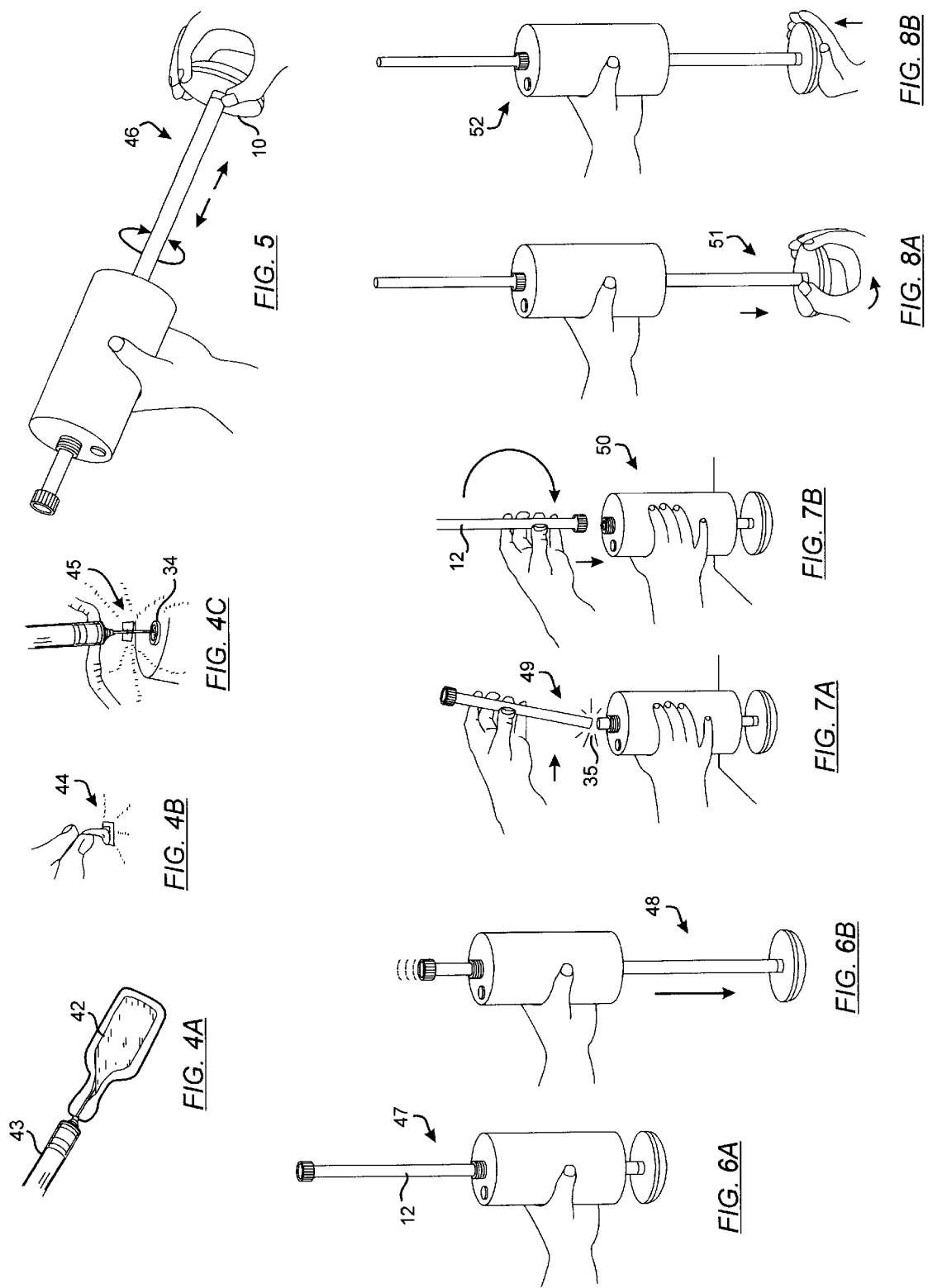

BONE CEMENT ISOVOLUMIC MIXING AND INJECTION DEVICE

FIELD OF THE INVENTION

This invention relates generally to methods for preparing and delivering a self-curing cement formed as a polymeric reaction product after mixing a powder polymer component with a liquid monomer component.

More particularly, the invention relates to methods and apparatuses for preparing and delivering bone cement in an operating room environment.

BACKGROUND OF THE INVENTION

In many orthopedic surgical procedures, it is necessary to employ a bonding material to set implants such as pins and artificial joints in bones. The cement employed for such surgical purpose is generally a polymeric material which is prepared by copolymerization of its components as needed. Because of the necessity for fairly quick setting material, the cement is almost universally prepared in the operating room environment and during the course of an operation. The preparation of the cement involves mixing the aforementioned components, evaluating the consistency of the mixture and injecting into the patient's tissues.

Care must be applied to create an homogeneous cement by thorough mixing of the components, and avoiding air bubbles. Sterility must be maintained both within the mixture itself, but also about the instruments used throughout the entire process. Care must be exercised not to contaminate the hands of the surgeon and his assistants.

The processing time, i.e., the time at the surgeon's disposal for carrying out all the required work to anchor a prosthesis in correct position in a bone cavity, from the beginning of the introduction of the cement into the bone cavity until the hardening of the cement that no longer permits any change in the position of the prosthesis, is relatively short. Consequently, the bone cement mixing and delivering apparatus must be operable in a minimum of time.

Motorized, table-top bone cement mixing machines such as the ones disclosed in U.S. Pat. Nos. 5,571,282 Earle, and 5,975,751 Earle, like any other electro-mechanical devices of this type, are very difficult to sterilize. The mere manipulation of their control switches and levers is likely to compromise the sterility of the operator's gloved hands. Moreover, this type of device fulfills only the preparation phase of the process and not the delivery of the cement into the bone cavity.

The process of transferring the bone cement from a mixture to a delivery device can be time-consuming and potentially contaminating. It is desirable to minimize the transfer to avoid contamination and save time. The most desirable method is to mix the components of the bone cement and deliver the final product into a bone cavity under an isobaric and isovolumic environment that will not draw in gases and contaminants into the bone cement.

Hand-operated devices combining bone cement mixing and injecting mechanisms have been proposed such as the one disclosed in U.S. Pat. Nos. 5,100,241 Chan; and 5,558,745 Tanaka et al. In those instruments, the components of the bone cement, prior to mixing, are kept in separate cartridges made of materials such as plastic that are not very suitable for the highly reactive monomer. The mixing occurs in non-isobaric and non-isovolumic environments and oftentimes under negative pressure relative to ambient atmosphere. Impurities may be drawn into the cement and partial evaporation of the monomer may create weakening bubbles in the cement.

None of those prior art devices provides a convenient way to test the viscosity of the cement, the surgeon must resort to rubbing a small bead of the cement between thumb and forefinger in order to access its consistency and viscosity.

The instant invention results from attempts to develop a more effective and practical method and apparatus for quickly and safely mixing the components of a bone cement, assess the viscosity of the resulting mixture, and inject it in a timely manner into a bone cavity.

SUMMARY OF THE INVENTION

The principal and secondary object of this invention are to provide a device and method for conveniently preparing and delivering a polymerized bone cement under sterile, isobaric and isovolumic conditions in an operating room environment while safeguarding the integrity of the operator's sterile apparel, avoiding the admission of impurities and the formation of weakening gas bubbles and providing a rapid and convenient way to assess the viscosity of the material prior to injection.

These and other valuable objects are achieved by packaging a volume of polymer powder in a sterilized and evacuated cylindrical vessel which contains a disk agitator mounted on a tubular axial shaft manipulable through an external handle, and a piston that can be selectively connected to the disk for translation by means of the same shaft and handle after the mixture has been thoroughly mixed. The vessel is packaged in a sterile and evacuated pliable envelope. The liquid monomer is drawn into a syringe then injected through the sterile envelope and an elastomeric, self-sealing diaphragm in the wall of the vessel. A tubular, distal portion of the shaft that passes through the outlet port can be broken off allowing the shaft to be withdrawn to open the outlet. The broken-off part can be mounted on a bushing surrounding the outlet to form a nozzle. The viscosity of the mixture can be assessed by letting the agitator and shaft move under their own weight through the mixture while the vessel is held in a vertical position.

BRIEF DESCRIPTION OF THE DRAWING

FIGS. 4A, 4B and 4C are detail perspective views of the monomer injecting step;

FIG. 5 is a perspective view of the mixing step;

FIGS. 6A and 6B are perspective views of the viscosity step;

FIGS. 7A and 7B are perspective views of the nozzle installation step;

FIGS. 8A, 8B and 8C are perspective views of the ejection step;

DESCRIPTION OF THE PREFERRED EMBODIMENT OF THE INVENTION

Figure 1:
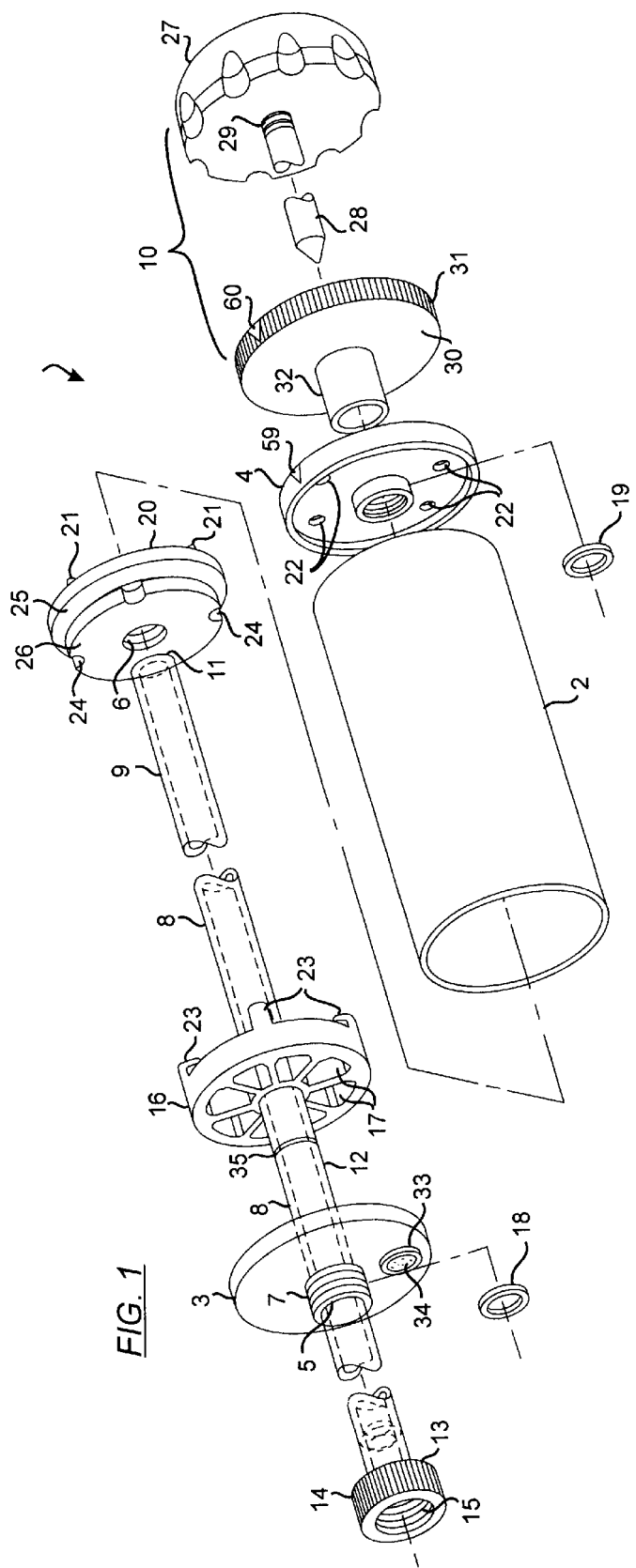
FIG. 1 is an exploded view of the mixing and ejecting device.

Referring now to the drawing, there is shown in FIG. 1, a device 1 that acts as both a mixer and as a injector for a polymeric cement. The device comprises a tubular, cylindrical vessel 2 including a first end wall 3 at the distal, axial end of the vessel, and a second end wall 4 at the proximal, axial end of the vessel. The two walls are hermetically bonded to the vessel. The first wall has an outlet 5 in its center that acts as a delivery port. The second wall has coaxial aperture 6. The outlet is surrounded by a bushing 7 having a threaded outer wall to form a first coupling member. A tubular shaft 8 is coaxially mounted through the vessel. The shaft comprises a first segment 9 passing through the aperture 6 and having a handle assembly 10 engaged into its proximal end 11 outside the vessel. A second segment 12 of the shaft having substantially the same length and cross-diameter as the first segment is engaged into the outlet 5. Its distal end 13 has a knurled flange or bushing 14 that has an inside threaded surface 15 to form a second coupling member matingly connectable to the first bushing coupling member 7. A agitator disk 16 is fixedly mounted on the shaft at the juncture of the distal end of the first segment and the proximal end of the second segment. The agitator disk 16 has a radius slightly smaller than the radius of the vessel. The agitator disk has a plurality of openings 17 therethrough. O-rings 18, 19 are mounted in the inner walls of the outlet 5 and the aperture 6 respectively in order to hermetically seal the vessel around the shaft. A piston 20 having an outer radius commensurate with the inside radius of the vessel is slidingly mounted on the first segment 9 of the shaft. A plurality of nibs 21 projecting from the back face of the piston are releaseably engaged in corresponding and substantially commensurate cavities 22 bored into the inside surface of the second wall 4. Accordingly, the piston 20 remains initially stationary and does not follow any axial or rotary movement of the shaft 8. By contrast, the disk agitator 16 which is fixedly mounted on the shaft, follows any rotary or axial movement of the shaft imposed to it by manipulation of the handle assembly 10. The piston can be coupled to the shaft by means of a bayonet-type mechanism comprising a plurality of angular nibs 23 mounted around the periphery of the disk agitator 16, and corresponding notches 24 in the periphery of the piston 20. Accordingly, the shaft can be withdrawn until the nibs 23 of the agitator are engaged into the notches 24 of the piston. By rotating the shaft and disk, the nibs move into the groove 25 constituted by the unnotched part of the piston frontal flange 26. Pushing the handle and shaft forward, after coupling the agitator to the piston, will disengage the piston from its mooring against the inside surface of the second wall and move it toward the first wall 3. The handle assembly comprises an hemispherical head 27, and a plunger rod 28 fixedly bonded to and projecting from the center of the head 27. The rod has an outer radius slightly smaller than the internal radius of the tubular shaft 8. The root 29 of the rod is threaded and screwed into the correspondingly threaded central bore of a disk 30 having an knurled peripheral wall 31 commensurate with the size of the head 27. A coaxial tubular flange bushing 32 is engaged upon, and permanently bonded to the proximal end of the first segment 9 of the shaft. Accordingly, the head and the rod 28 can be unscrewed and separated from the disk 30 and the shaft 9.

A window 33 cut into the first wall 3 mounts a flexible diaphragm 34 made from elastomeric material. The diaphragm is thick enough to be self-sealing after having been transpersed by a syringe needle. The diaphragm is flexible enough to respond to small pressure differences between inside and outside the vessel.

A narrow crease line 35 in the outside or inside wall of a proximal end section of the shaft second segment creates a weak point about which the shaft can be broken.

Figure 2:
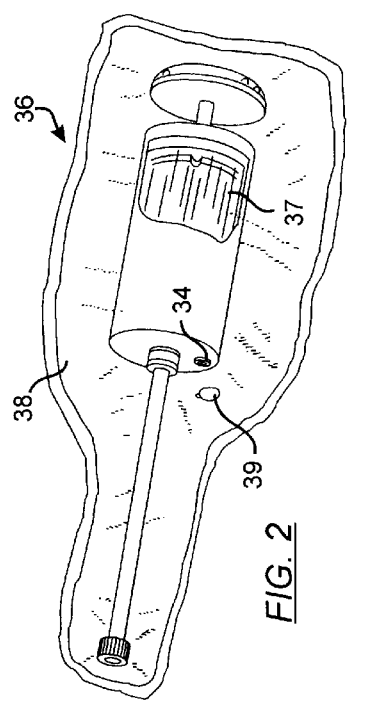
FIG. 2 is a perspective view of the device in a first type of packaging.

In a first type of packaging 36 illustrated in FIG. 2, the device 1 containing a volume of polymeric powder 37 is sterilized and packaged into evacuated envelope 38 made of pliable sheet material. A small zone proximate the position of the diaphragm 34 is sterilized and covered with a protective patch 39.

Figure 3:
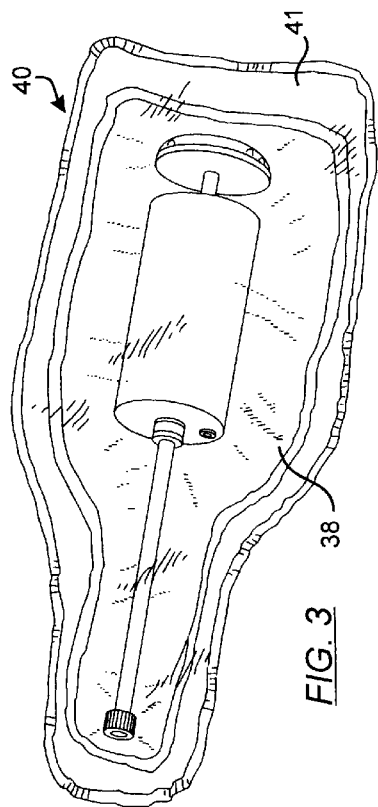
FIG. 3 is a perspective view of the device in a second type of packaging.
Figure 8C:
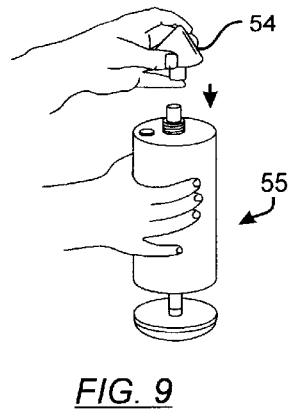
Figure 9:
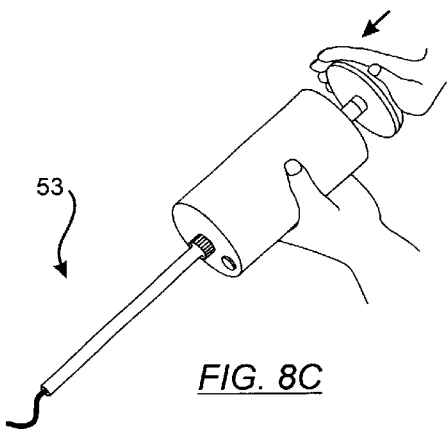
FIG. 9 is a perspective view of the installation of a pressure fitting.
Figure 10A:
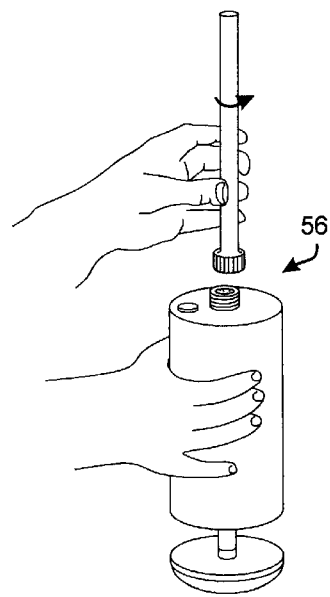
FIGS. 10A, 10B and 10C are perspective views of the nozzle cleaning step for recovery residual cement.
Figure 10B:
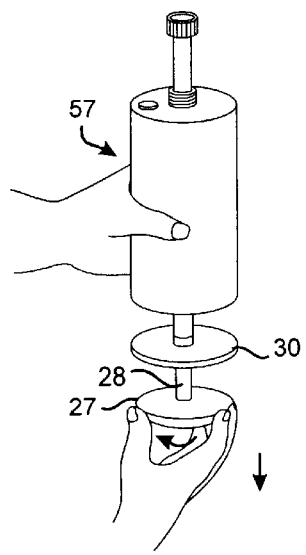
Figure 10C:
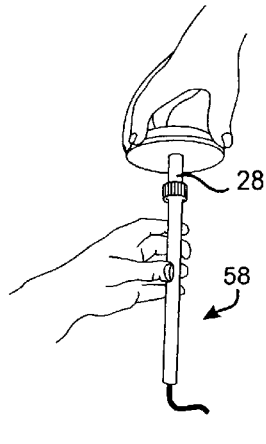

In a second type of packaging 40 illustrated in FIG. 3, the entire outer surface of the envelope 38 is sterilized, and the entire structure is encased into a sterile enclosure 41.

Referring now to FIGS. 4–10, the method of using the device 1 in the preparation and injection of a polymeric bone cement will be described.

A sterile volume of liquid monomer sufficient to form a self-curing compound when mixed with the volume 37 of polymeric powder is drawn from its vial 42 into a sterile syringe 43. When the first type of packaging is used, the protective patch 39 is removed 44 from the surface of the envelope 38, and the needle of the syringe is inserted 45 through the sterile zone of the envelope and through the diaphragm 34. The differential pressure between the ambient atmosphere and the inside of the vessel draws the liquid monomer from the syringe until the outer and inner pressures equilibrate. If necessary, additional liquid monomer can be force-injected into the vessel by pressing upon the piston of the syringe.

When the second type of packaging is used, the outside enclosure is open and discarded exposing the entire sterile outer surface of the envelope 38. The needle of the syringe is then injected through the envelope and the diaphragm and the process of monomer injection is continued as discussed in connection with the first type of packaging.

In a second step, after removal and disposal of the envelope 38, the polymeric components are thoroughly mixed by manipulating 46 the handle and shaft through repetitive axial and rotational movements which forces the cement components to pass through the openings of the disks.

At any time after mixing, the viscosity of the bone cement can be directly estimated by noting the speed at which the disk agitator translates from an upper position 47 near the first wall of the vessel to the lowermost position 48 near the piston and the second wall of the vessel when the device is held in a vertical position with the handle below the vessel. The faster the descent of the agitator and shaft, the lower the viscosity of the cement. Markings along the shaft 8 may be provided to help the user quantify the rate of shaft translation. The head 27 is preferably weighted to optimize the viscosity measurement process. Once the cement has cured to the desired degree of viscosity, the handle and shaft are moved inwardly toward the outlet and the most distal segment of the shaft protruding through the first wall bushing is broken 49 about its crease line 35. The broken part is turned around 50 and fitted upon the bushing to form a nozzle. The handle is pulled back opening the outlet 5 and bringing the disk agitator into contact with the piston. By pulling and twisting the handle 51, the piston is attached to the disk agitator through the bayonet-type locking mechanism described earlier. External markings 59, 60 on the peripheral edges of the second wall 4 and the disk 30 are provided in order to facilitate correct alignment of the agitator and piston into their interlocking relative positions. Pushing forward upon the handle 52, will cause the piston to leave its mooring against the second wall of the vessel and translate toward the first end wall pushing the cement 53 out of the delivery port and nozzle. A pressure fitting 54 may be mounted 55 on the bushing in lieu of the above-described nozzle.

After the vessel has been fully emptied under the push of the piston, the small amount of cement remaining in the nozzle can be flushed out by using the handles' rod. The nozzle is decoupled from the vessel 56. The head and rod are separated 57 from the knurled disk and tubular shaft. The rod is then inserted 58 into the proximal end of the nozzle to ream out the remaining bone cement.

While the preferred embodiment of the invention has been described, modifications can be made and other embodiments may be devised without departing from the spirit of the invention and the scope of the appended claims.

What is claimed is:

1. A device for preparing and injecting a polymeric bone cement under isobaric and isovolumic conditions, said device comprising:
   a tubular vessel including a first axial end wall having an outlet, a second axial end wall opposite said first axial end wall and having an aperture;
   a shaft having a first segment engaged into said aperture and including a proximal end section outside said vessel and a distal end section inside said vessel; and
   a second segment having a proximal section inside said vessel and a distal section passing through and projecting beyond said outlet and having a distal end outside said vessel;
   an agitator secured to the distal section of said first segment and to the proximal section of said second segment;
   a piston coaxially and slidingly engaged upon said first segment inside said vessel; and
   means for selectively locking said piston to said agitator;
   whereby the volume occupied by the shaft during axial translation within the vessel remains substantially constant.

2. The device of claim 1, which further comprises:
   a handle mounted at the proximal end of said first segment;
   a bushing coaxially mounted in said first wall around said outlet and including a first coupling member outside said vessel;
   a second coupling member at the distal end of said second segment;
   said second coupling member being matingly connectable to said first coupling member; and
   said second segment being tubular;
   whereby the distal section of said second segment can be broken into two parts, and its distal end can be mounted upon said bushing by way of said coupling member.

3. The device of claim 1, wherein said vessel further comprises a wall zone made of elastomeric material capable of self-sealing after having been punctured by a syringe needle.

4. The device of claim 3, which further comprises a volume of polymer powder held under vacuum in said vessel.

5. The device of claim 4, which further comprises a sealed and evacuated envelope, made of pliable sheet material, hermetically surrounding said vessel and shaft.

6. The device of claim 5, wherein the interior of said envelope and its contents are sterilized.

7. The device of claim 6, wherein said envelope further comprises a sterile outer zone, and a protective releasable patch covering said outer zone.

8. The device of claim 5, which further comprises:
   a hermetically sealed, discardable housing containing said envelope; and
   wherein the inside of said housing and its contents are sterilized.

9. The device of claim 1, wherein said agitator comprises a disk having at least one opening therethrough.

10. The device of claim 1, wherein said means for selectively locking comprises a bayonet mechanism including at least one nib mounted on said agitator, and at least one notch connectively compatible with said nib, on said piston.

11. A device for preparing and injecting a polymeric bone cement under isobaric and isovolumic conditions, said device comprising:
    a tubular vessel including a first axial end wall having an outlet, a second axial end wall opposite said first axial end wall and having an aperture;
    a shaft having a first segment engaged into said aperture and including a proximal end section outside vessel and a distal end section inside said vessel, and a second tubular segment including a proximal section inside said vessel and a distal section engaged into said outlet and having a distal end;
    an agitator secured to the distal section of said first segment and to the proximal section of said second segment;
    a piston coaxially and slidingly engaged into said first segment inside said vessel;
    means for selectively locking said piston to said agitator;
    a handle mounted at the proximal end of said first segment;
    a bushing coaxially mounted in said first wall around said outlet and including a first coupling member outside said vessel; and
    a second coupling member at the distal end of said second segment, said second coupling member being matingly connectable to said first coupling member;
    whereby said second segment can be broken into two parts, and its distal end can be mounted upon said bushing by way of said coupling member.

* * * * *